(12) United States Patent
Gregg

(10) Patent No.: US 12,376,778 B2
(45) Date of Patent: Aug. 5, 2025

(54) ECG FEATURES FOR TYPE AHEAD EDITING AND AUTOMATIC UPDATE FOR REPORT INTERPRETATION

(71) Applicant: KONINKLIJKE PHILIPS N.V., Eindhoven (NL)

(72) Inventor: Richard E Gregg, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 697 days.

(21) Appl. No.: 14/899,764

(22) PCT Filed: Jun. 9, 2014

(86) PCT No.: PCT/IB2014/062065
§ 371 (c)(1),
(2) Date: Dec. 18, 2015

(87) PCT Pub. No.: WO2014/203114
PCT Pub. Date: Dec. 24, 2014

(65) Prior Publication Data
US 2016/0135700 A1 May 19, 2016

Related U.S. Application Data

(60) Provisional application No. 61/836,189, filed on Jun. 18, 2013.

(51) Int. Cl.
| | |
|---|---|
| *A61B 5/339* | (2021.01) |
| *G06F 3/0481* | (2022.01) |
| *G06F 3/0484* | (2022.01) |
| *G06F 3/0489* | (2022.01) |
| *G06F 40/166* | (2020.01) |

(52) U.S. Cl.
CPC ............ *A61B 5/339* (2021.01); *G06F 3/0481* (2013.01); *G06F 3/0484* (2013.01);
(Continued)

(58) Field of Classification Search
CPC ........ G16H 10/00; G16H 15/00; G16H 20/00; G16H 30/00; G16H 40/00; G16H 50/00;
(Continued)

(56) References Cited

U.S. PATENT DOCUMENTS

| | | |
|---|---|---|
| 4,989,610 A | 2/1991 | Patton et al. |
| 5,614,331 A | 3/1997 | Takeuchi et al. |

(Continued)

FOREIGN PATENT DOCUMENTS

| | | |
|---|---|---|
| EP | 1406198 A2 | 7/2004 |
| JP | 2000123098 A | 4/2000 |

(Continued)

OTHER PUBLICATIONS

Roy, S., et al. "Location-Aware Type Ahead Search on Spatial Databases: Semantics and Efficiency" SIGMOD '11. Jun. 2011. (12 Pages).

*Primary Examiner* — Robert W Morgan
*Assistant Examiner* — Charles P Coleman

(57) ABSTRACT

An electrocardiogram (ECG) device includes a processor (114), a memory (116) coupled to the processor and an interface (120) configured to generate an edit window and configured to permit user input in the edit window. A type ahead module (124) is stored in the memory and is responsive to input entered in the edit window. The type ahead module is configured to predict a next word, phrase, interpretation code or category being input by a user based on a subset of alphanumeric key strokes and a context probability associated with a list of possible ECG entries. A report review and edit module (128) may also be stored in the memory. The report review and edit module is configured to update a severity of an ECG report based upon current ECG interpretation statements and rules in accordance with an access or edit operation by an operator.

7 Claims, 7 Drawing Sheets

(51) Int. Cl.
  *G06F 40/274* (2020.01)
  *G06N 7/01* (2023.01)
  *G16H 15/00* (2018.01)
  *G16H 40/63* (2018.01)
(52) U.S. Cl.
  CPC .......... *G06F 3/0489* (2013.01); *G06F 40/166* (2020.01); *G06F 40/274* (2020.01); *G06N 7/01* (2023.01); *G16H 15/00* (2018.01); *G16H 40/63* (2018.01)
(58) Field of Classification Search
  CPC ........ G16H 70/00; G16H 80/00; G16H 10/40; G16H 20/10; G16H 20/13; G16H 20/17; G16H 40/63; A61B 5/044; G06F 3/0481; G06F 3/0484; G06F 3/0489; G06F 17/24; G06F 17/276; G06N 7/005; G06Q 50/22–24
  USPC .................................................... 705/2, 3, 20
  See application file for complete search history.

(56) References Cited

U.S. PATENT DOCUMENTS

| | | | |
|---|---|---|---|
| 6,004,276 | A | 12/1999 | Wright et al. |
| 6,223,077 | B1 | 4/2001 | Schweizer et al. |
| 6,377,965 | B1 | 4/2002 | Hachamovitch et al. |
| 6,556,864 | B1 | 4/2003 | Picardo et al. |
| 6,968,227 | B2 | 11/2005 | Macadam et al. |
| 2001/0033953 | A1 | 10/2001 | Gan et al. |
| 2002/0082825 | A1 | 6/2002 | Rowlandson et al. |
| 2003/0028368 | A1 | 2/2003 | Grandy et al. |
| 2003/0088275 | A1 | 5/2003 | Palmer et al. |
| 2003/0120311 | A1 | 6/2003 | Hansen |
| 2004/0051721 | A1 | 3/2004 | Ramseth |
| 2004/0054294 | A1* | 3/2004 | Ramseth ................ G16H 40/40 600/509 |
| 2004/0054296 | A1 | 3/2004 | Ramseth |
| 2004/0133244 | A1 | 7/2004 | Vaisnys et al. |
| 2006/0161066 | A1* | 7/2006 | Elion .................... A61B 5/044 600/509 |
| 2007/0166617 | A1 | 7/2007 | Gozdz et al. |
| 2015/0282726 | A1* | 10/2015 | Grube ................... A61B 5/316 600/523 |

FOREIGN PATENT DOCUMENTS

| | | |
|---|---|---|
| JP | 2004148105 A | 5/2004 |
| JP | 2009223560 A | 10/2009 |
| JP | 2010167045 A | 8/2010 |
| WO | WO2004010323 A2 | 1/2004 |
| WO | WO2012059854 A1 | 5/2012 |

* cited by examiner

ECG FEATURES FOR TYPE AHEAD EDITING AND AUTOMATIC UPDATE FOR REPORT INTERPRETATION

BACKGROUND

1. Technical Field

This disclosure relates to medical instruments and more particularly to electrocardiographic equipment and interpretation/editing of inputs and outputs.

2. Description of the Related Art

An electrocardiograph (e.g., a 12-lead diagnostic device) generates a report called an electrocardiogram. An electrocardiograph (ECG) signal is a 10 second snapshot of the electrical activity of the heart. The electrocardiogram or ECG report includes patient demographics and ECG interpretation in text format on top of a piece of paper with the ECG signal trace shown on a portion of the paper. The orientation of the paper is generally landscape.

Hospitals typically employ electrocardiographs, also called cardiographs, which feature automated analysis of the ECG by software algorithms. The algorithms make measurements of the ECG signal and provide an interpretation of the ECG report through an analysis of the ECG measurements. The interpretation is a set of statements, one statement per line, which describe clinical conditions that can be detected from ECG measurements. Under this interpretation, a severity is included, which is an overall summary of the ECG interpretation. The severity is basically "normal" or "abnormal" with some variations between normal and abnormal.

A common workflow for ECG reports in a hospital can include the following. A clinician orders an ECG test. An ECG technician or nurse records the ECG on the patient. An ECG report is generated by the cardiograph including an automated ECG interpretation. The ECG report is transmitted to an ECG management system. The ECG interpretation is reviewed, corrected and electronically signed by an ECG expert. The review and correction involves adding or deleting existing statements for ECG interpretation such as "Sinus rhythm", "Acute myocardial infarction", etc. In addition to editing the interpretation, the ECG expert needs to update the severity which appears as "normal ECG" or "abnormal ECG". Other clinicians involved with the patient's care review the ECG report along with other test results to come up with a diagnosis consistent with their symptoms and test results.

One problem is the tendency of ECG readers to focus on the ECG interpretation and neglect to update the severity. One example of a mistake is when an ECG interpretation with an abnormal statement leads to a severity of abnormal, but the abnormal statement was not correct due to a mitigating factor. The ECG expert could correct the interpretation, but because direct action is needed to switch the severity from abnormal to normal, the expert may inadvertently or otherwise not change the severity to the correct interpretation. This may cause issues down the line, e.g., a treating physician may initiate an unnecessary cardiology consult because the ECG was listed as abnormal.

Another issue with ECG devices includes inefficiencies in inputting text data. Some ECG systems employ a tool that reduces a long list of text choices to a very short list with the entry of just one or two characters that start the word or phrase desired. This is similar to the idea of auto-completion or auto-correction where a user types part of a word or phrase and the computer selects a match or gives a set of likely options that contain the text the user has typed. In the choice of ECG interpretation statement when editing a 12-lead diagnostic ECG, typing characters in the statement code can zero in on the desired statement quickly. However, a problem arises in that there are many choices that have similar text and similar statement codes, making alphabetic ordering alone insufficient and giving raise to human error in selecting a code.

SUMMARY

In accordance with the principles of the present invention, an exemplary electrocardiogram (ECG) device is provided and described herein which includes a processor, a memory coupled to the processor and an interface configured to generate an edit window and configured to permit user input in the edit window. A type ahead module is stored in the memory and is responsive to input entered in the edit window. The type ahead module is configured to predict a next word, phrase, code or category being input by a user based on a subset of alphanumeric key strokes and a context probability associated with a list of possible ECG entries.

Also in accordance with the principles of the present invention, another exemplary electrocardiogram (ECG) device is provided and described herein which includes a processor, a memory coupled to the processor and an interface configured to generate an edit window and configured to permit user input in the edit window. A report review and edit module is stored in the memory. The report review and edit module is configured to update a severity of an ECG report based upon current ECG interpretation statements and rules stored in the memory and triggered in accordance with an access or edit operation by an operator.

Further, in accordance with the principles of the present invention, an exemplary method for automatic severity updating for an electrocardiogram (ECG) is provided and described herein which includes providing an ECG interpretation based upon ECG testing; triggering a review and edit application upon accessing the ECG interpretation; reviewing the ECG interpretation statement by statement against a predetermined set of rules; and automatically updating a severity of an ECG report based upon the ECG interpretation statements and the rules.

Further still, in accordance with the principles of the present invention, an exemplary method for type ahead prediction in an electrocardiogram (ECG) device is provided and described herein which includes preparing ECG features by determining a probability for conditions under consideration for diagnosis by an ECG; sorting the ECG features by probability to present most likely conditions or abnormalities that a patient may have; and presenting ECG interpretation statements in probability order in an editing application based on a context, the ECG features and a subset of alphanumeric key strokes entered by an operator.

The method can further include re-ordering (412) the ECG interpretation statements based on the probability upon a user editing action. Presenting can include predicting a next word, phrase, code or category being input by a user based on the context of the ECG features and the subset of alphanumeric key strokes entered by the operator. Determining the probability can include loading precalculated probabilities from a database or computing the probability given an ECG waveform and existing measurements. It is also possible that presenting ECG interpretation statements includes presenting ECG interpretation statements in probability order in an editing application based on a context, historic data, the ECG features and a subset of alphanumeric key strokes entered by an operator. The historic data can include a frequency of selection of ECG interpretive statements by the operator. The context can include a type of test or set of tests being performed, a regression of ECG related features from a collection of records, a set or use of patient fiducials, a location of a test and/or an operator of the test.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
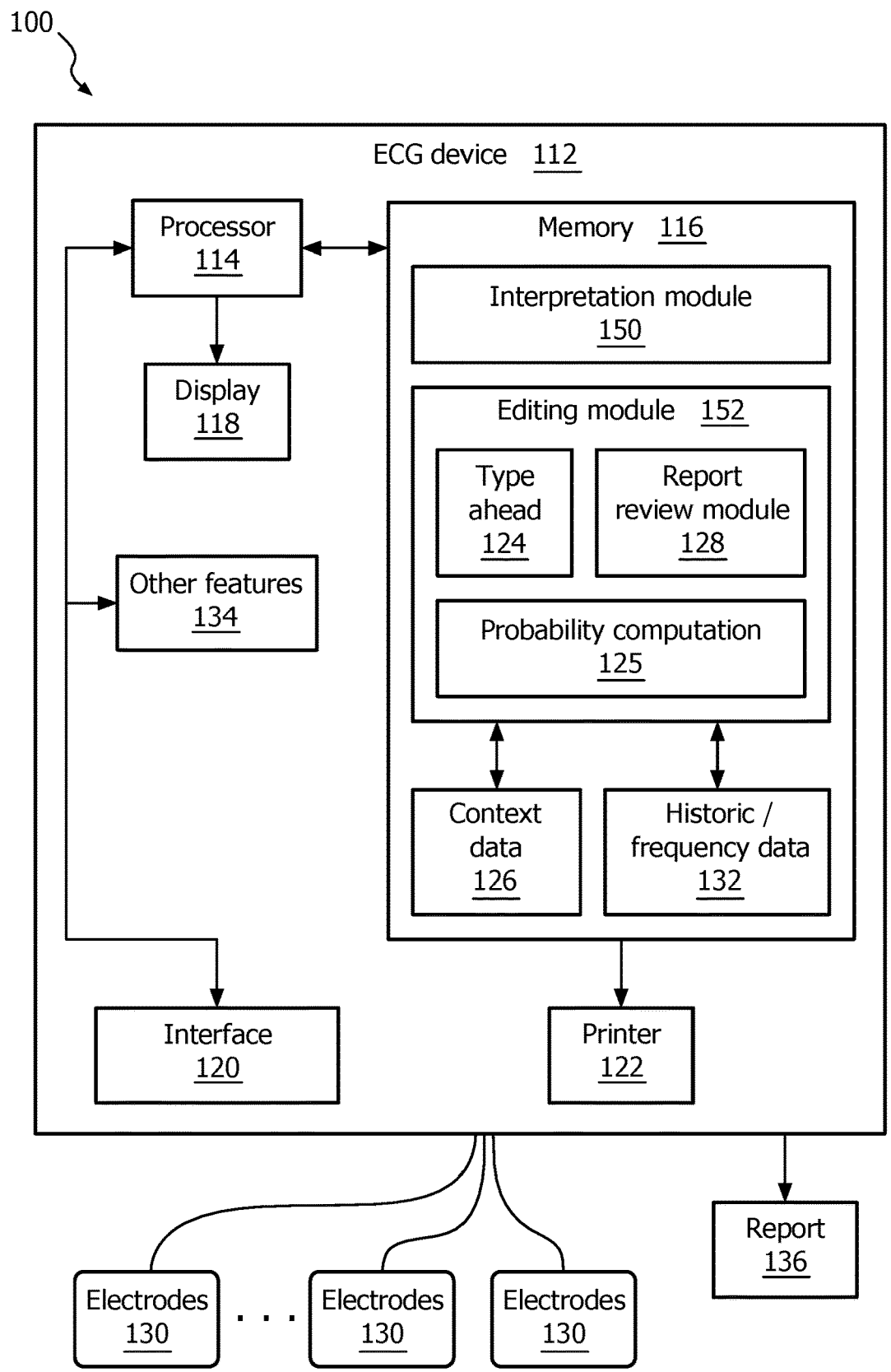
FIG. 1 is a block/flow diagram showing an electrocardiogram (ECG) device in accordance with illustrative embodiments.

In accordance with the principles of the present invention, exemplary embodiments of electrocardiograph (ECG) devices and methods for employing such devices are provided and described herein. The ECG devices include enhanced input and output mechanisms to speed up electronic editing, improve reporting accuracy and reduce user error. In one embodiment, a type ahead module is employed to reduce a long list of choices to a very short list while employing input characters, historic data and ECG measurement basis (e.g., context) to zero in on the desired statement more quickly. This reduces the available choice space by providing context-based options. Alphanumeric order of type ahead does not get to the answer fast enough. ECG measurement basis can get to the correct answer faster and with greater accuracy.

Correct detection of the ECG abnormalities present in a particular ECG may be based on the correct placement of fiducials on the parts of the ECG waveform. Fiducials define the start and end of each part of the ECG waveform including the P-waves, QRS complexes, and T-waves. The duration between the fiducials for the QRS complex, the start and the end of the QRS, is called the QRS duration. The QRS duration is one important aspect in the interpretation of many conduction system abnormalities such as right bundle branch block (RBBB) or left bundle branch block (LBBB). If the fiducials are not placed correctly by computer analysis, the RBBB or LBBB abnormalities will not be detected. Moving the fiducials to the correct location on the ECG waveform and using those fiducial locations to re-measure the ECG can result in the interpretation changing from incorrectly missing the abnormality to correctly detecting an abnormality. In one embodiment, by moving fiducials or by making a fiducial selection using, e.g., a touch screen to move the fiducials, context-based data (updated ECG measurements) can be provided to reduce the choice space for a type ahead function.

In other embodiments, frequency of usage by the user or a set of users may be employed to improve the success rate in providing the desired statement with the least amount of typing. Alphabetic order, frequency of interpretation statement usage, context usage (when ECG specific features are used), etc. may all be employed to provide a predicted probability for each interpretation statement when electronically editing an ECG. The predicted probability or context probability may be computed based upon one or more of these factors, e.g., with an application-specific probability derived from the ECG features, i.e., when a specific ECG feature indicates high probability, a particular interpretation statement is frequently chosen.

In another embodiment, an automated ECG interpretation module is employed to update an overall severity. The ECG interpretation is made up of a set of statements such as, e.g., "Sinus rhythm" or "Acute myocardial infarction." The severity is a summary of the ECG interpretation that appears on a report as, e.g., "Normal ECG" or "Abnormal ECG". The clinical consumers of the ECG report throughout the hospital—as opposed to the ECG expert reading the ECG— often rely on that severity without understanding the fine points of the ECG interpretation. The ECG interpretation module automatically updates to the overall severity as the person editing an ECG deletes and inserts statements in the interpretation since the severity depends on the entire ECG interpretation.

It should be understood that the present invention will be described in terms of medical instruments; however, the teachings of the present invention are much broader and are applicable to text based input and/or report based output devices. In some embodiments, the present principles are employed in tracking or analyzing complex biological or mechanical systems. In particular, the present principles are applicable to tracking or diagnostic procedures for biological systems including procedures in all areas of the body such as the lungs, heart, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, an ECG system 100 is illustratively shown in accordance with one embodiment. System 100 may include an ECG device or workstation 112 from which ECG measurements or tests are taken and supervised. Workstation 112 preferably includes one or more processors 114 and memory 116 for storing programs and applications. Memory 116 may store an electrocardiogram editing system 152, which includes one or more modules that permit a user to edit an ECG report 136. The editing system includes a type ahead module 124 configured to interpret key strokes or input data to reduce input entry time, a probability computation module (or abnormality prediction module) 125 that computes probabilities for ECG terms (or other terms depending on the application), and a report review and edit module 128 that analyzes and adjusts severity automatically and based on a complete picture of the ECG report 136.

The type ahead module 124 selects codes for ECG terms. In accordance with one embodiment, the type ahead module 124 employs context data 126 and historic data 132 and associated probabilities stored in memory 116 (and/or computed by the probability module 125) to determine a next word, phrase, code or category that is needed in a text field in an edit application for an ECG.

The type ahead module 124 takes a longer list of choices and reduces the list to a very short list of prioritized choices with the entry of each character at an interface 120. In the choice of diagnostic ECG interpretation where the number of statements to choose from approaches, e.g., 600, typing characters in a statement code can zero in on the desired statement quickly except that many statement codes start with similar letters. Using application specific ECG features stored in the context data 126 in addition to frequency of usage (historic data 132) by a particular user or group of users and alphanumeric prediction, a diagnostic ECG interpretation field can easily, accurately and quickly be filled-in.

In one embodiment, the type ahead module 124, when adding or replacing a statement by code (for instance, the statement "sinus rhythm" is represented by the code "SR"), will go alphabetically and by ECG feature. An importance function is stored in the type ahead module 124 and is based on ECG features and secondarily by alphabetic order. Parallel lists can also be offered, one based primarily on alphabetic order and the second based primarily on ECG feature. ECG features can be based on commonly used ECG criteria such as, e.g., left ventricular hypertrophy (LVH) voltage by Cornell criteria to say what the probability of LVH is for the ECG in question.

A partial list of ECG measurements/features for use in editing type ahead may include the following, non-exhaustive list:
1) Left ventricular hypertrophy: Cornell LVH voltage=lead aVR R-wave amplitude+lead V3 S-wave amplitude;
2) Recent myocardial infarction: Selvester QRS score;
3) Acute myocardial infarction: sum of ST-segment deviation;
4) Left bundle branch block: fuzzy logic QRS duration AND posterior horizontal QRS axis;
5) Right bundle branch block: fuzzy logic QRS duration AND anterior terminal QRS axis;
6) $2^{nd}$ degree AV block: group beating, i.e., repeating pattern of RR intervals, short, short, long, short, short, long, with a 2:1 or 3:1 or 4:1 pattern;
7) $3^{rd}$ degree AV block: uniform random PR intervals; etc.

Further refinements can be provided for a frequency of usage computation from the historic data 132. Frequency of usage can be personalized to a user or a group of users. In addition, frequency of change can drive the list so that any frequent change from one diagnostic statement to another can put the result statement at the top of the list each time the original statement appears.

The type ahead module 124 works with a graphical user interface, which may be included in the interface 120 to generate a pop-up menu in a display 118. The menu may include suggested statement changes when measurements are updated. In one embodiment, suggestions may be generated by the type ahead module 124 based on a new measurement value and a change in the measured value between what was there previously and a value provided by the user.

In another embodiment, movement of a fiducial point marker (See FIG. 2) by the user automatically forces a re-measure of the ECG complex and a proposed change to the interpretation by an automated interpretation algorithm/module 150 in the ECG device 112. This changes the context in which the measurements are made, which results in an update of the probability computation module 125, which calculates probability of abnormalities using ECG feature predictions based on the context data 126. In one embodiment, marking some of the P-waves, F-waves or pacemaker spikes as a starting pattern causes the automated interpretation algorithm 150 to use the user selection to detect remaining waves by shape and timing and then offer a new interpretation. This also changes the context in which the measurements are made, which results in an update of the abnormality prediction module's 125 predictions based on the context data 126. By simply moving fiducials (172-180, FIG. 2) manually or virtually (e.g., using a touch screen, etc. to move fiducials) can provide a new analysis and a correct or current interpretation that sets the context data 126 to be more relevant to a specific scenario. This reduces the need for editing each piece of information separately as the predictions of abnormality prediction module 125 will be more accurate.

The present principles are particularly useful in electronic editing of ECG morphology, ECG rhythm and pacemaker rhythm field in an ECG report 136. The type ahead module 124 may make predictions using Baysian probability-based ECG interpretations to score the most likely entry, although other techniques may be employed.

The memory 116 also stores the report review and edit module 128 configured to analyze a report 136 output from the device 112 and determine whether a status change is warranted or needed and then make the appropriate status change in accordance with a reviewer's input and supervision.

The report review and edit module 128 reads ECG interpretations in the report to determine severity based on an entire ECG interpretation. One simple example would be for the overall severity to be set equal to the worst severity of the individual interpretation statements since each statement in the interpretation has its own severity. Based upon best practices or predetermined criteria (rules), the module 128 can determine overall severity and may call an ECG abnormal if there are a certain number of statements (ECG interpretations that are called "otherwise normal", which is a severity somewhere between normal and abnormal). The module 128 for severity may run and update the severity each time a statement is added, deleted or changed by the editing ECG expert in the report 136.

The ECG device 112 includes the display 118 for viewing the report 136 and may include or show other data or provide an interface for controlling or managing the ECG device 112. Display 118 may also permit a user to interact with the ECG device 112 and its components and functions, or any other element within the system 100. This is further facilitated by the interface 120 which may include a keyboard, mouse, a joystick, a haptic device, or any other peripheral or control to permit user feedback from and interaction with the ECG device 112. The ECG device 112 preferably includes a printer 122 for outputting the report 136 or other pertinent information. The ECG device 112 may include other features and capabilities 134, such as alarms, power connections, other software features, etc.

The ECG device 112 includes a plurality of electrodes (or leads) 130 to be connected to a patient for taking measurements. The number and type of electrodes 130 may vary depending on the application, device and testing protocol.

Figure 2:
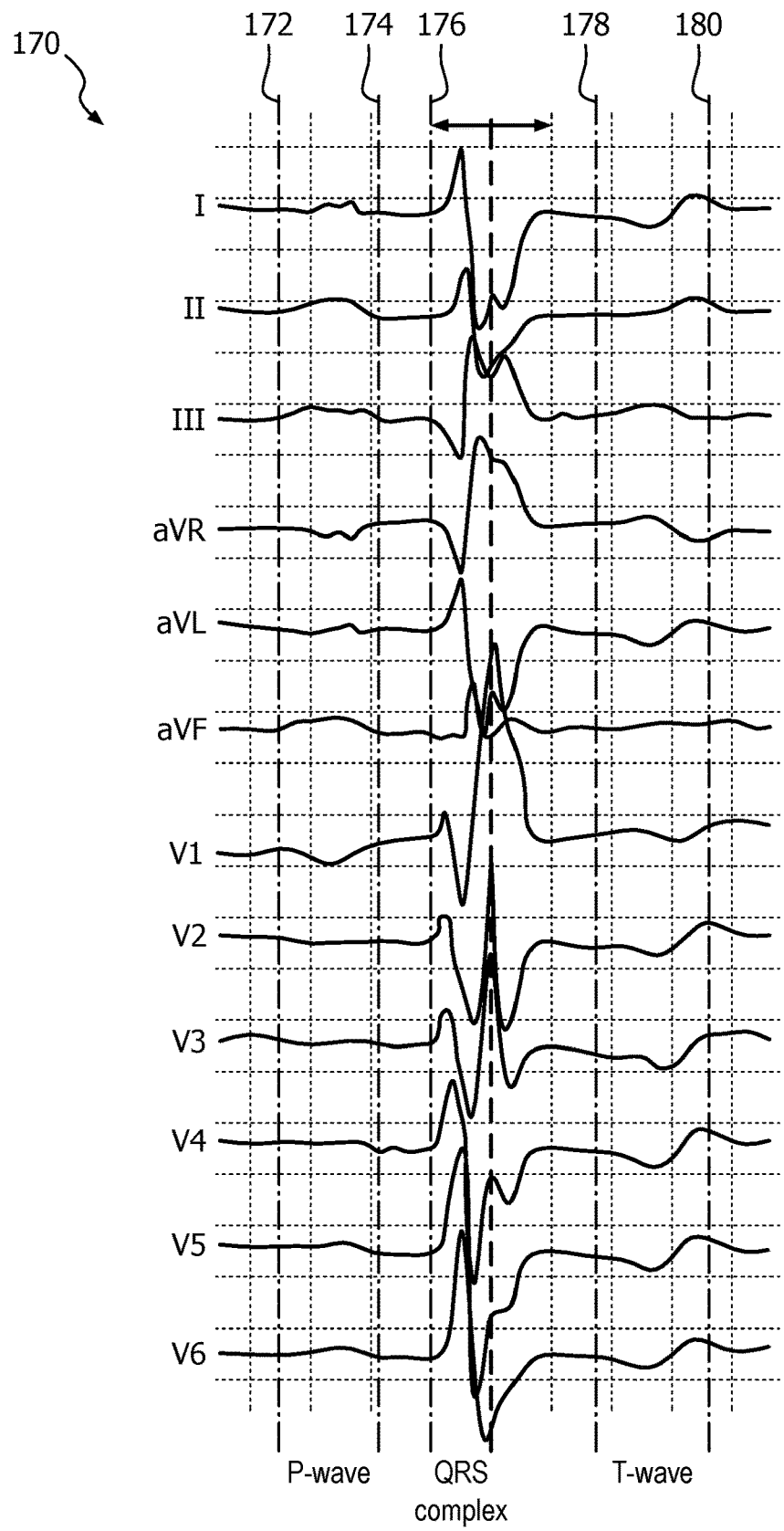
FIG. 2 is an electrocardiograph or electrocardiogram showing fiducial placement and movement in accordance with the editing system to demonstrate the present principles.

Referring to FIG. 2, a plot 170 of a representative heart beat is made up of an averaged PQRST complex for each of leads I, II, III, aVR, aVL, aVF, V1, V2, V3, V4, V5, V6. A P-wave is found between the first two vertical dotted lines 172 and 174. These lines 172, 174 are fiducials for the P-wave. A T-wave lies between the last two fiducials 178, 180 (vertical dotted lines), and a QRS complex lies between middle fiducials 176, 178. An ST-segment lies between the end of the QRS and the beginning of the T-wave. In this example, the fiducial marking the end of the QRS complex is incorrect. Correct placement would be to the right at the common inflection point of the signal in all leads before the signal approximates a straight line. That nearly straight line is the ST-segment.

In accordance with the present principles, a fiducial presentation of this type for the representative beat includes an ability to move the fiducials (172-180) to provide a better or more correct placement on the waveform relative to the fiducials (172-180). The fiducial locations compared to the representative beat waveform is an input to the automated ECG analysis which then uses these corrected fiducials to re-measure, re-interpret and re-calculate the ECG features to arrive at better probability estimates for likely abnormalities like, e.g., LBBB, RBBB or LVH as computed by the probability computation module 125.

Figure 3:
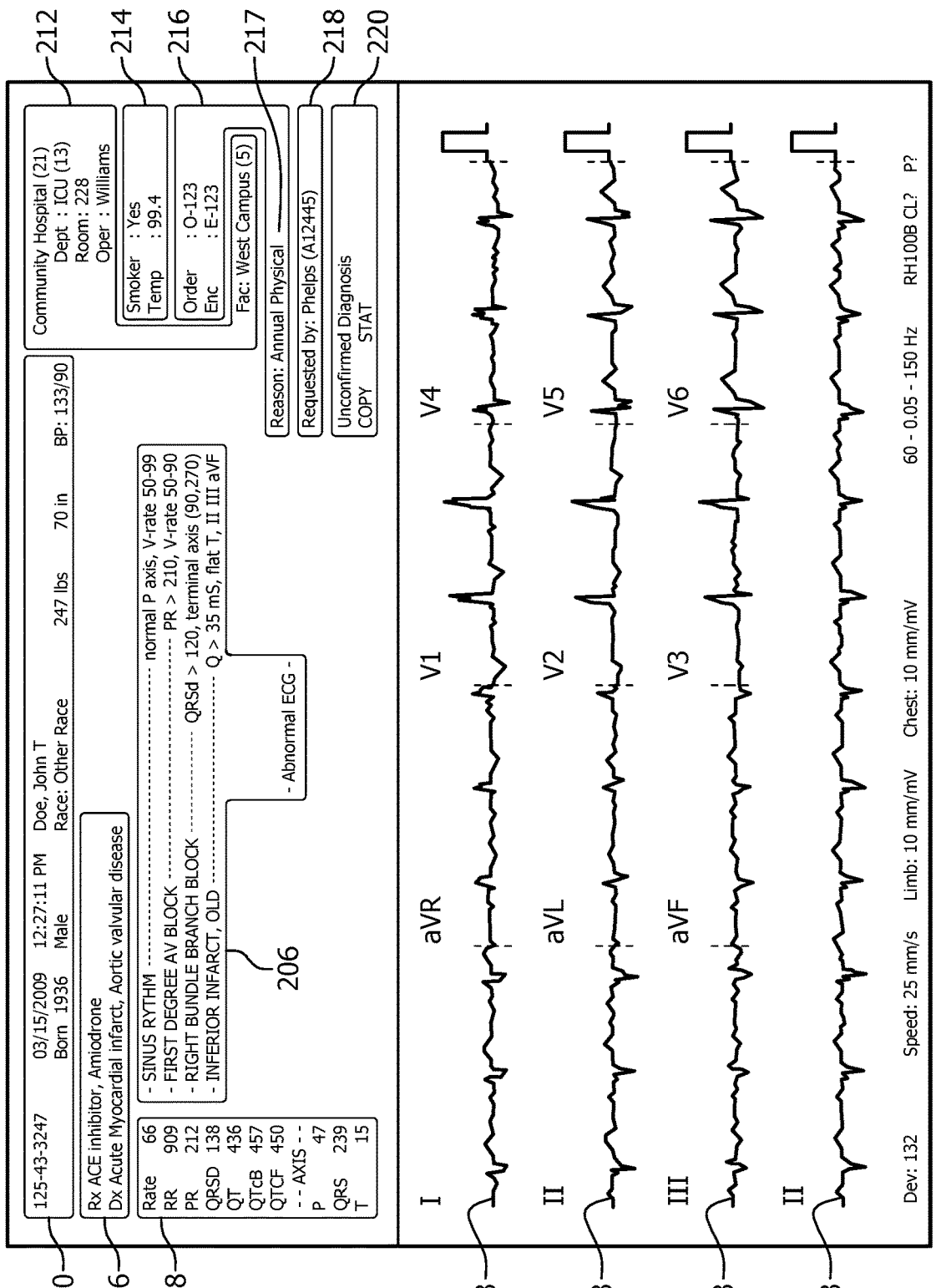
FIG. 3 is an electrocardiograph or electrocardiogram editing system showing a standard diagnostic ten second 12-lead ECG report to demonstrate the present principles.

Referring to FIG. 3, a standard diagnostic ten second 12-lead ECG report 200 (see report 136, FIG. 1) is shown to demonstrate the present principles. The diagnostic report 200 includes computer generated ECG interpretation, which is found in a box 206. The overall severity is found at the bottom of box 206. Information found in box 206 is the part that is typically corrected by a cardiologist (edited). A cardiologist would "read" the ECG, interpret the ECG and edit the computer interpretations listed in box 206. The user can click on any line and delete it or the user can insert a new line from a canned list. When inserting a new line, a pop up window is generated including a probability-ordered subset of the canned list that applies with the highest probability to the particular ECG being edited as described with respect to FIG. 1.

The report 200 includes a graph section 202 with one or more signal traces 203 that measure electrical activity of a heart. The report 200 may include personal data fields that provide patient and time data 210, hospital/location data/ operator data 212, patient specific measurement data 214, index/facility data 216, reason for test data 217, requesting physician data 218, test status data 220, drug/medication data 226, and other data. Heart rate, and commonly used intervals, durations and angular axes such as PR interval, P-wave duration, QRS duration, QT interval, P-wave axis, QRS axis and T-wave axis are provided in box 208. Note that any or all of these data fields may be configured to employ the type ahead features of the present embodiments as described herein.

Figure 4:
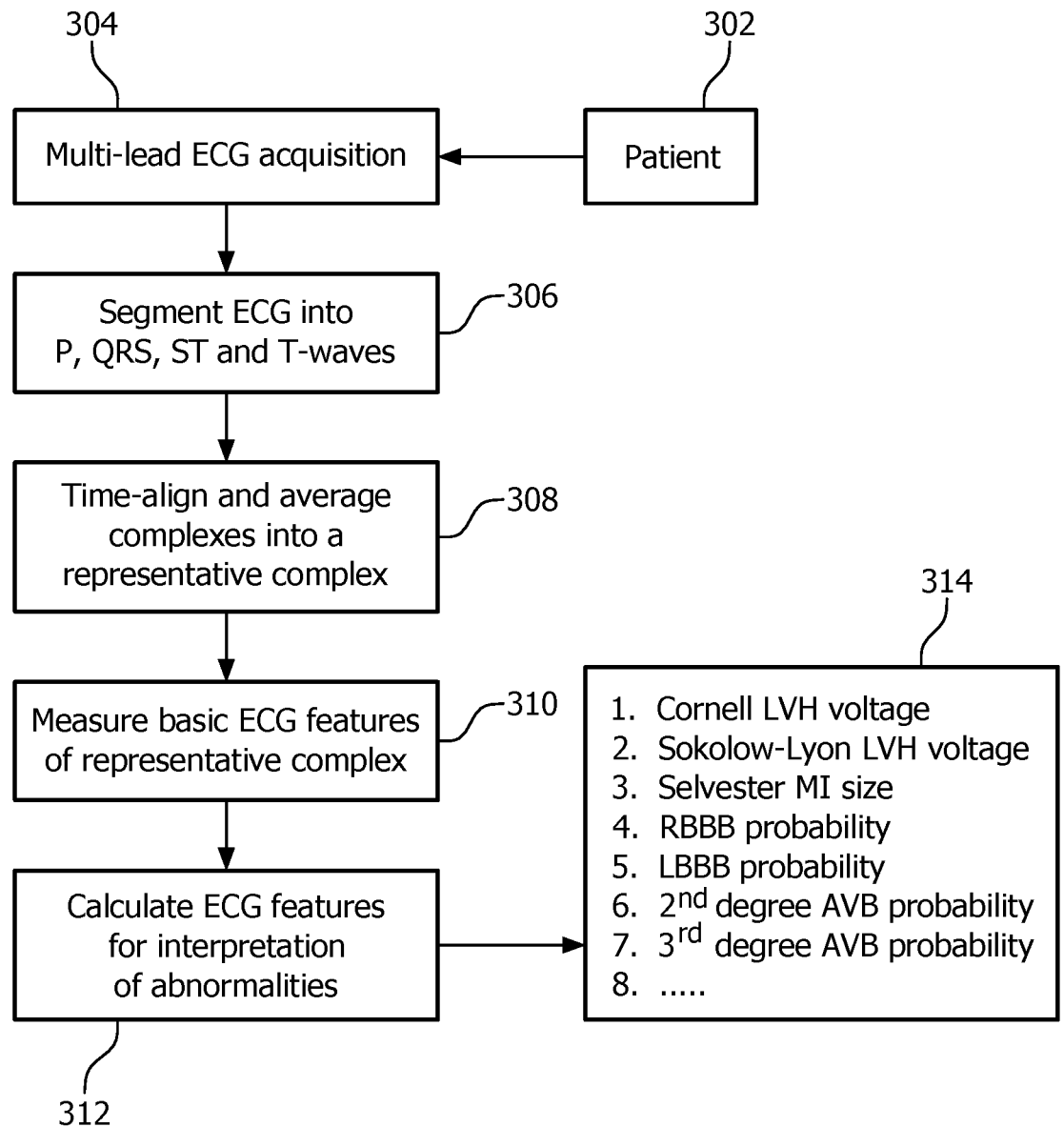
FIG. 4 is a block/flow diagram showing a system/method for calculating ECG interpretation probabilities to be employed in accordance with the present principles.

Referring to FIG. 4, a block/flow diagram shows preparation and use for a ten second 12-lead ECG in accordance with one embodiment. The ECG is acquired and analyzed in preparation for editing by a clinician. Only the computation of ECG features is described here; however, the present capabilities can be extended to other test fields or data fields. Typically, automated ECG analysis also includes interpretation of the ECG. The interpretation part of the computer algorithm is not shown in FIG. 4. In block 302, electrodes are applied to a patient's skin, e.g., on left-chest, ankles, wrists, etc. Wires connect the electrodes to the ECG acquisition hardware. In block 304, an ECG acquisition is performed. Electronics needed to turn the heart's electrical signal into a multichannel digital waveform snapshot for computer processing is performed.

In block 306, ECG is segmented. This determines each location of the electrical indication of a heart beat in the digital waveform. Since a normal resting heart rate is around 75 beats per minute, the heart beats will occur roughly once per second. As is known, the QRS, ST segment and T-wave represent the electrical activity of the ventricles while the P-waves represent the electrical activity of the atria. In block 308, time alignment and averaging complexes are performed to determine a representative complex. This includes snipping all similar heart beats or complexes out of the signal, time aligning them on top of each other and averaging them together to come up with a low-noise average complex for further processing.

In block 310, basic measurements are made on the representative complex. This includes measuring the averaged representative complex according to FIG. 5 to get estimates of the QRS duration, QT interval, etc. Block 310 can also accept waveform location input, "fiducials", relative to the representative complex to improve the basic ECG measurements. In block 312, diagnostic ECG features are computed. From the basic measurements, derived measurements are calculated such as, e.g., probability of left ventricular hypertrophy (LVH). These are the measures which are employed for interpretation; high probabilities mean the condition, LVH in this example, is likely present. Possible interpretations are illustratively listed in block 314.

Figure 5:
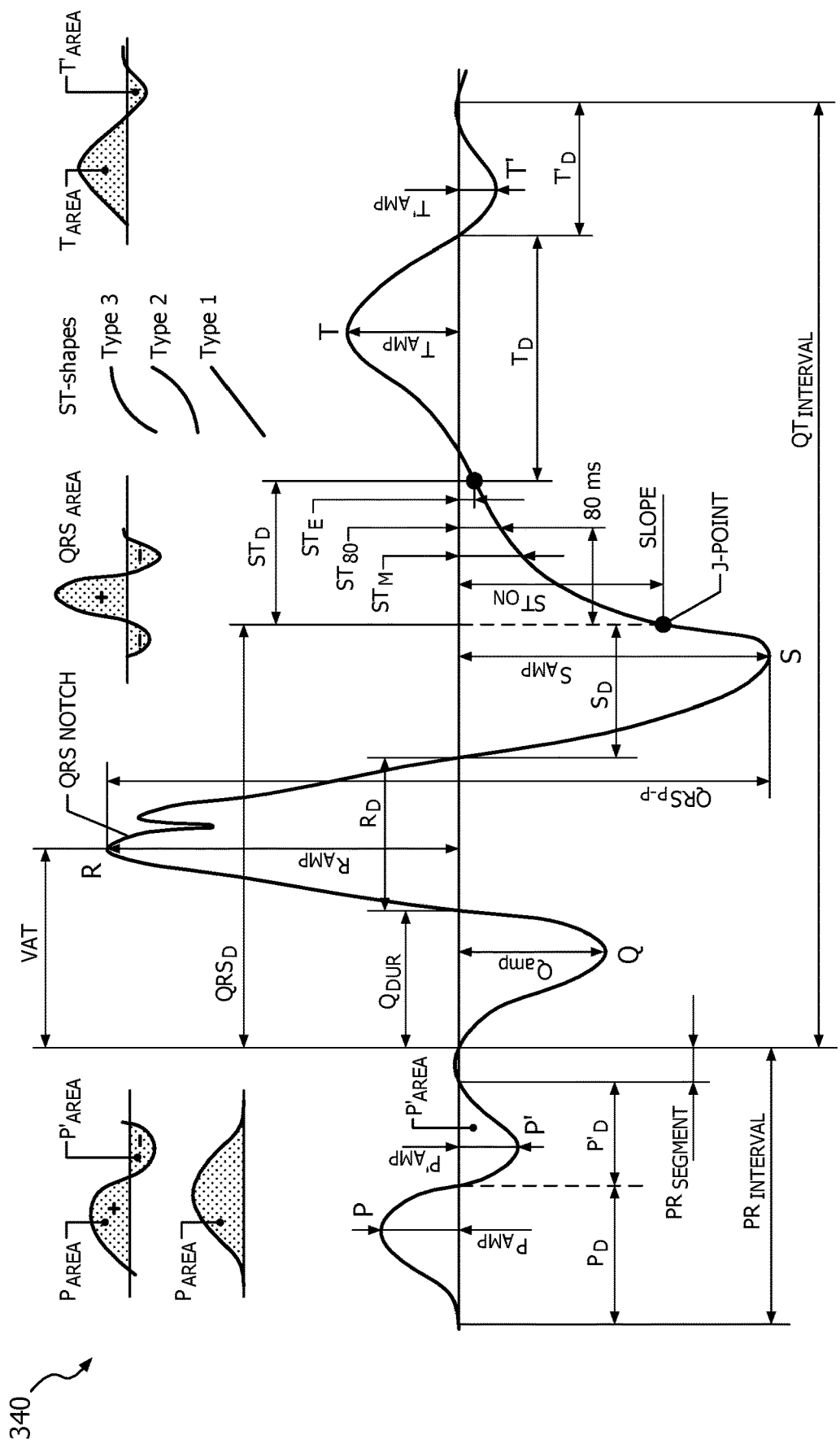
FIG. 5 is a plot showing basic ECG measurements as measured on a representation complex for an ECG to be employed in accordance with the present principles.

Referring to FIG. 5, a representative complex 340 is shown and is subject to interpretation in accordance with the present principles. The representative complex 340 shows a plurality of variables and measurements that are computed or measured on the representative complex. All basic measurement variables depicted in FIG. 5 are known and will not be described here for simplicity.

Figure 6:
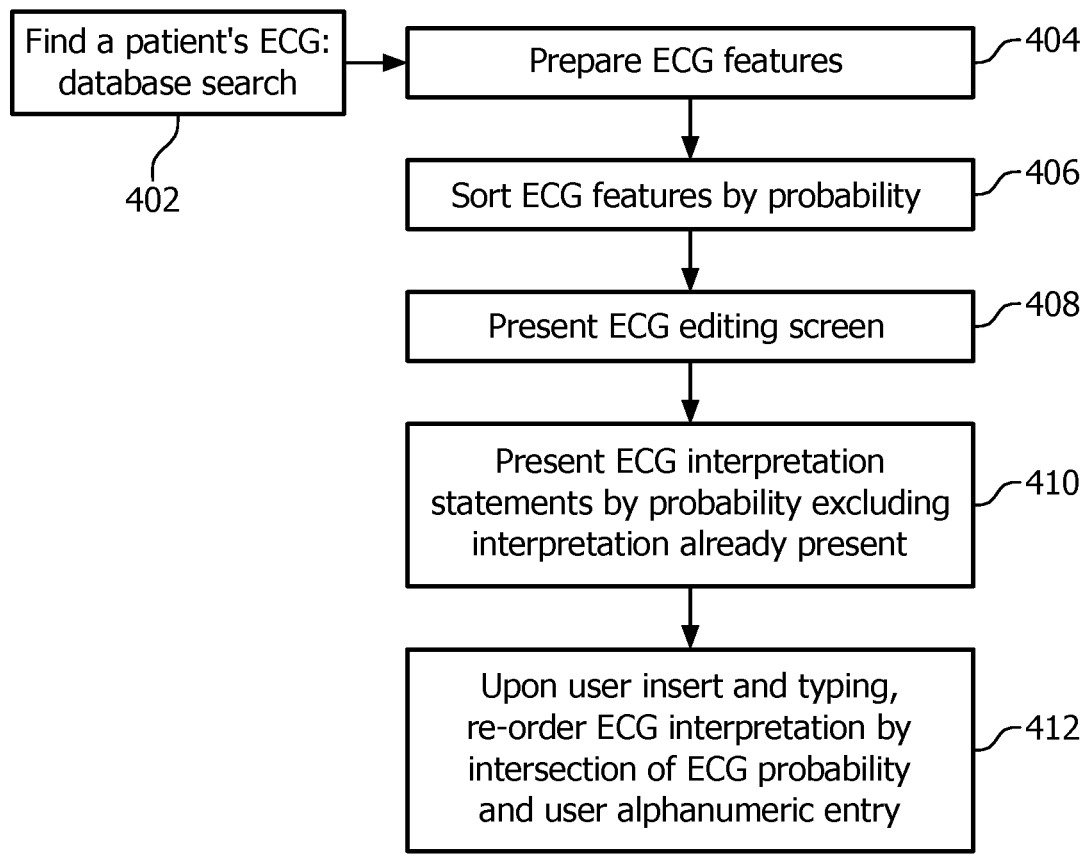
FIG. 6 is a block/flow diagram showing a system/method for type ahead services for an ECG device in accordance with the present principles.

Referring to FIG. 6, a block/flow diagram shows steps for the type ahead module 124 (FIG. 1) in accordance with one illustrative embodiment to assist a user in an editing process. In block 402, a clinician reviews all the non-urgent ECGs taken in the hospital that day. For small hospitals, one clinician could read and correct all the ECGs for a day. For larger hospitals, multiple clinicians are assigned to read and correct ECGs each day. A search is made for a patient's ECG in a database given a list of ECGs to read or a patient who's ECG would help with a diagnostic decision. An ECG is found in the database and presented to the clinical user in a computer application for editing ECGs. The clinician looks at the ECG to determine the rhythm first (heart rate and regularity or irregularity of the rate). Next, the clinician looks at the shape of the P, QRS and T-waves to detect abnormalities that can be seen from the ECG shape. In block 404, ECG features are prepared by calculating the probability of all conditions under consideration like sinus rhythm, atrial fibrillation, ventricular tachycardia, LVH, LBBB, RBBB and other conditions commonly diagnosed by ECG. Pre-calculated probabilities are obtained from a database or calculated on the fly given the ECG waveform and existing basic measurements (e.g., by the probability computation module 125, FIG. 1). The type ahead module 124 may be employed to either calculate or retrieve the ECG features from the database.

In block 406, the type ahead module 124 then orders the list of possible interpretation statements by probability. Each line of the interpretation is a "canned" interpretation statement generated by an automated ECG analysis. Statements that are already in the interpretation are not included in the list. All ECG features are sorted by probability to present the most likely conditions/abnormalities that the patient may have.

In block 408, the patient's ECG is presented in an editing application. In block 410, the ECG interpretation statements are presented in probability order, preferably in a separate window, based on ECG features and the clinician's favorite interpretive statements or other context information. The ECG statements listed in probability order may be provided in the editing window so that the user is presented with options/predictions based on the user's input.

In block 412, upon a user editing action like "insert", the ECG interpretation statements are re-ordered based on ECG features, the typed text and other factors. For example, if the user starts typing (type ahead or auto-completion), the combination of the characters typed to make a word appropriate to ECG interpretation and the probability based on ECG features result in a reordering of the ECG interpretation statements in a pop-up window. In one embodiment, there may be two windows, one for statement abbreviations or codes and one window for the full statements. The codes may be reordered using type ahead technology modified in accordance with the present principles. For example, alphanumeric factors, frequency factors and context factors are employed to recompute or define probabilities/predictions based on the context or other factors being employed. These factors may be employed in the re-ordering of interpretation statements or other statements/input. The context factor, e.g., may include a probability that the reading clinician will actually use each statement in question. Since each clinician may have their own preferred set of interpretation statements, this factor helps their favorite statements appear at the top of the list of applicable statements. In another embodiment, given a set of tests called for, a location within the hospital, e.g., intensive care, etc., the title or position of the person conducting the test, etc. can all be factored into the weighting or probability for ordering of terms in the look ahead feature.

Figure 7:
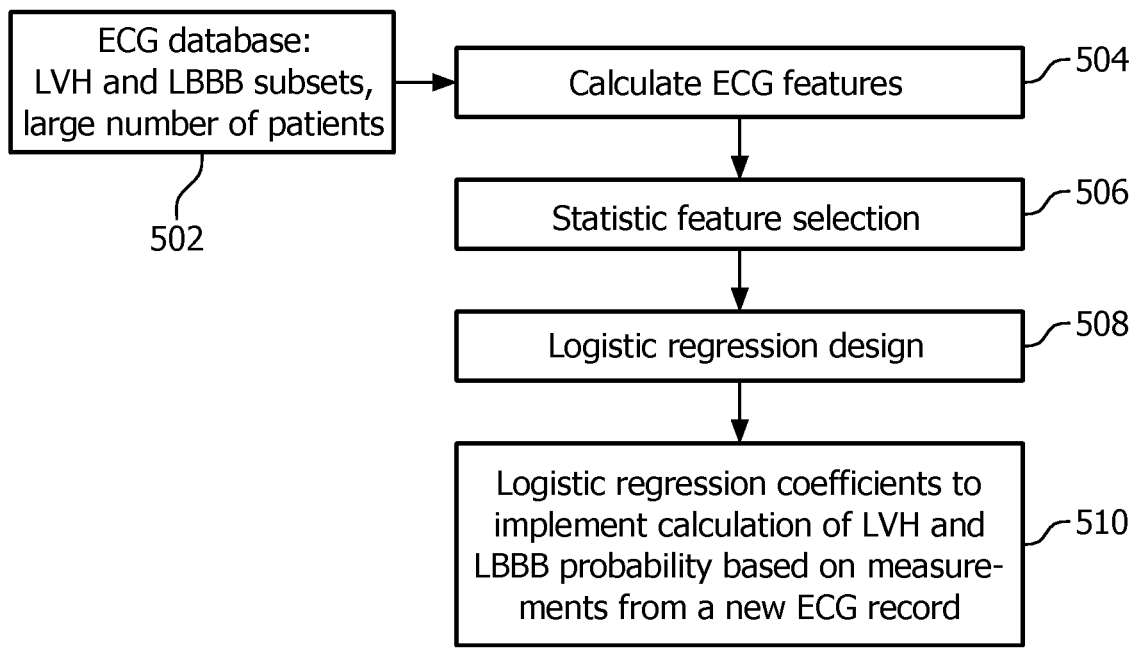
FIG. 7 is a block/flow diagram showing a system/method for assigning probabilities to ECG features in accordance with the present principles.

Referring to FIG. 7, a block/flow diagram shows steps for an example of how ECG features are created for use in ordering ECG interpretation statements in the text ahead application. Left ventricular hypertrophy (LVH) and left bundle branch block (LBBB) are often confused in automated ECG analysis (and even when a cardiologist reads an ECG report) so they should be considered together to allow for accurate discrimination between the two. Many other areas of ECG interpretation are similar and create points of confusion as well. The LVH and LBBB feature will be employed in this example.

In block 502, an ECG database is provided and preferably includes a large number of patients. To design the ECG features to determine the probability of LVH or LBBB, the database of ECGs is processed to compute parameters often associated with LVH and LBBB. The ECG database needs annotations for each ECG indicating whether it is a case of LVH, LBBB or some other condition. In block 504, using pattern recognition techniques for feature selection, the parameters most strongly associated with LVH and LBBB would be used in a logistic regression model for LVH and LBBB. In block 508, the logistic regression model is designed for LBBB and LVH and takes the strongly associated parameters (calculated from basic ECG measurements) as inputs to provide probability estimates for the likelihood of LVH and LBBB. If the LVH probability were high, e.g., near 1.0, for a particular ECG, the LVH interpretive statement would be high in the list of likely abnormalities. These probability estimates for LVH and LBBB would make up just two of many ECG features used to order interpretation statements based on likelihood.

In block 510, logistic regression coefficients are computed to implement computations of LVH and LBBB probabilities based on measurements from a new ECG record. This data is input to the context data 126 in memory 116 of FIG. 1.

Figure 8:
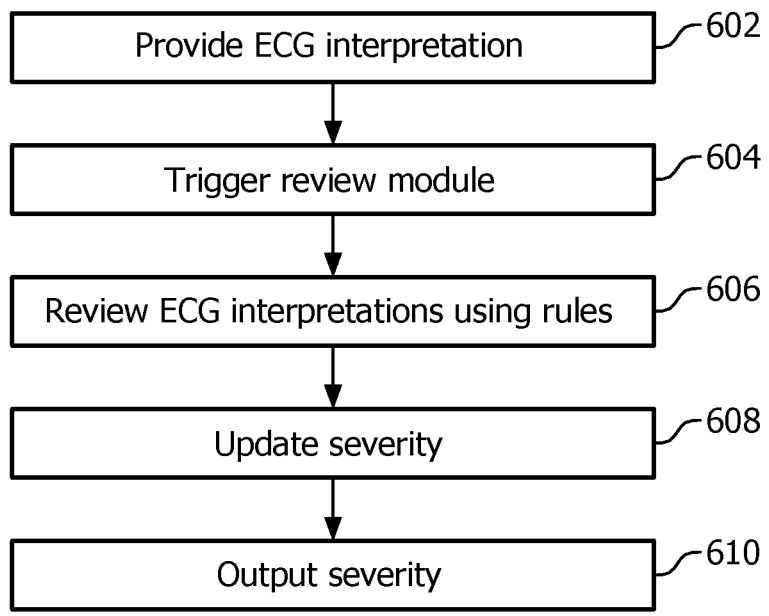
FIG. 8 is a block/flow diagram showing a system/method for automated severity updating for ECG reports in accordance with the present principles.

Referring to FIG. 8, a block/flow diagram shows steps implemented by the report and review module 128 (FIG. 1). In block 602, an ECG interpretation is provided to the module 128 after a test. In block 604, the module 128 is triggered by access to ECG interpretations by a clinician. In block 606, the module 128 reviews the ECG interpretations looking for an interpretation statement or set of interpretation statements that will change the severity from normal to abnormal or vice versa.

For example, the module 128 may determine severity is based on the entire ECG interpretation or the collection of statements, since each statement in the interpretation has its own severity. That is, two or more interpretation statements that otherwise provide a normal severity may be interpreted as an abnormal severity due to the plurality of interpretation statements. In another example, the severity may be set equal to a worst severity of the interpretations. In another example, overall severity may be changed calling an ECG abnormal if there are a certain number of statements that are called "otherwise normal", which is a severity somewhere between normal and abnormal. During the review in block 606, the module consults a rule set to determine whether the conditions exist to change the severity.

In block 608, the module 128 updates the severity each time a statement is added, deleted or changed by the editing ECG expert. In block 610, a report is output with the updated severity.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for ECG features for type ahead editing and automatic update for report interpretation (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An electrocardiograma, comprising:
a plurality of electrodes/leads for generating ECG signals indicative of an electrical activity of a heart;
an interface configured to generate an edit window and configured to permit user input in the edit window; and
a non-transitory memory encoded with modules for execution by a processor, wherein the modules include;
an ECG interpretation module including instructions stored in the non-transitory memory and executable by the processor to generate an automatic interpretation of an ECG report derived from the ECG signals; and
a type ahead module interactive with an editing, via user input in the edit window, of the interpretation of the ECG report automatically generated by the ECG interpretation module,
wherein the type ahead module including instructions stored in the non-transitory memory and executable by the processor to predict and display a next word, phrase, interpretation code or category interactively responsive to a subset of alphanumeric key strokes entered in the edit window for an editing of the interpretation of the ECG report automatically generated by the ECG interpretation module, and
wherein the instructions of the type ahead module to predict the next word, phrase, interpretation code or category type ahead module are derived from a context probability associated with a list of possible ECG entries interactively generated from the subset of alphanumeric key strokes.

2. The electrocardiogramecited in claim 1, wherein the context probability includes a type of test or set of tests being performed as a factor.

3. The electrocardiogramn claim 1, wherein the context probability includes a regression of ECG related features from a collection of records as a factor.

4. The electrocardiogramavice as recited in claim 1, further comprising:
adjustable fiducials stored in the memory and having a configuration executable by the processor to recompute the context probability.

5. The electrocardiogramecited in claim 1, wherein a factor of the context probability includes one of a location of a test and an operator of the test.

6. The electrocardiogramas recited in claim 1, further comprising:
historic data stored in the memory to provide one of a frequency and a manner of use for the list of possible ECG entries to influence the predictions of the type ahead module.

7. The electrocardiograma as recited in claim 1, wherein the editing, via the user input in the edit window, of the interpretation of the ECG report automatically generated by the ECG interpretation module includes one of an addition, a deletion or a change of an ECG interpretation statement.

* * * * *